(12) United States Patent
Chen et al.

(10) Patent No.: US 7,189,417 B2
(45) Date of Patent: Mar. 13, 2007

(54) NANOMETER-SIZED CARRIER MEDIUM

(75) Inventors: I-Wei Chen, Swarthmore, PA (US);
Hoon Choi, Bryn Mawr, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 466 days.

(21) Appl. No.: 10/427,242

(22) Filed: May 1, 2003

(65) Prior Publication Data

US 2003/0206859 A1 Nov. 6, 2003

Related U.S. Application Data

(60) Provisional application No. 60/376,794, filed on May 1, 2002.

(51) Int. Cl.
*A61K 9/50* (2006.01)
(52) U.S. Cl. .................. 424/501; 424/9.1; 424/489; 424/400; 514/772; 514/782; 977/773; 977/776; 977/831
(58) Field of Classification Search ............... None
See application file for complete search history.

(56) References Cited

U.S. PATENT DOCUMENTS

| 4,243,692 A | 1/1981 | Scholze et al. |
|---|---|---|
| 4,642,207 A | 2/1987 | Uda et al. |
| 5,128,081 A | 7/1992 | Siegel et al. |
| 5,486,675 A | 1/1996 | Taylor et al. |
| 5,514,349 A | 5/1996 | Parker et al. |
| 5,732,704 A | 3/1998 | Thurston et al. |
| 5,814,550 A | 9/1998 | Wolcott |
| 5,851,507 A | 12/1998 | Pirzada et al. |
| 5,876,683 A | 3/1999 | Glumac et al. |
| 6,205,352 B1 | 3/2001 | Carroll |
| 6,207,229 B1 | 3/2001 | Bawendi et al. |
| 6,225,198 B1 | 5/2001 | Alivisatos et al. |
| 2002/0053557 A1 | 5/2002 | Peterson et al. |

OTHER PUBLICATIONS

Derwent-All-No: 1989-116210 (1989).*
U.S. Appl. No. 10/668,484, filed Sep. 22, 2003, Shastri et al.
W. Stober, A. Fink and E. Bohn, "Controlled Growth of Monodisperse Silica Spheres in the Micron Size Range", J. Colloid Interface Sci., 26, 62-69 (1968).
M. Atik, P. DeLima Neto, L.A. Avaca, M.A. Aegerter, J. Zarzycki, "Protection of 316L Stainless Steel Against Corrosion by $SiO_2$ Coatings", J. Mater. Sci. Lett. 13 1081-1085 (1994).

(Continued)

*Primary Examiner*—Michael P. Woodward
*Assistant Examiner*—Eric E. Silverman
(74) *Attorney, Agent, or Firm*—Caesar Rivise

(57) ABSTRACT

The present invention relates to a colloidal dispersion of amine-terminated silica particles having a narrowly controlled size range in an aqueous phase for use in diagnostic imaging, drug delivery and gene therapy, as well as methods for preparing surface-modified silica particles suitable for use in an aqueous colloidal carrier medium, for preparing a diagnostic or therapeutic agent for targeted delivery to specific anatomical structures of a patient, and for performing a diagnostic or therapeutic procedure by administration to a patient of at least one diagnostic or therapeutic agent coupled with a colloidal dispersion.

24 Claims, 6 Drawing Sheets

OTHER PUBLICATIONS

K. Yoshida, K. Kamada, K. Sato, R. Hatada, K. Baba, M. Atsuta, "Thin Sol-Gel-Derived Silica Coatings on Dental Pure Titanium Casting", J. Biomed. Mater. Res. 48: 778-785 (1999).

D.C.L.Vasconcelos, J.A.N. Carvalho, M. Mantel, W.L. Vasconcelos, "Corrosion Resistance of Stainless Steel Coated with Sol-Gel-Silica", 273 135-139 (2000).

E.P. Plueddemann, "Silane Coupling Agents", Plenum Press, New York, Chapter 3, 49-73 (1982).

K.C. Vrancken, K. Possemiers, P. Van Der Voort, E.F. Vansant, "Surface Modification of Silica Gel with Aminoorganosilanes", Colloids and Surfaces, 98 235-241 (1995).

Wise, Donald L. ed., Handbook of Pharmaceutical Controlled Release Technology, Marcel Dekker Incorporated, New York, New York, pp. 329-344 (2000).

Niwa et al., Controlled Rel., (25), 89-98 (1993).

Murakami et al., Intl. J. Pharm., (187), 143-152 (1999).

Jiang, et al., Langmuir, 7, 2607-2615. (2002).

Xia et al. in Chemical Reviews 1999, 99, pp. 1823-1848.

Morrison and Ross, Colloidal Dispersion: Suspensions, Emulsions and Foams (Wiley Publ. 2002).

Tesoro et al., Silane and Other Coupling Agents, pp. 215-228 (1992).

Peng, J. Am. Chem. 2001: 123183.

A. van Blaaderen and A. Vrij, "Synthesis and Characterization of Colloidal Dispersions of FluorescenT Monodisperse Silica Spheres", Langmuir, 8 [12], 2921-2931 (1992).

A.E. Hawley, L. Illum and S.S. Davis, "Lymph Node Localisation of Biodegradable Nanospheres Surface Modified with Poloxamer and Poloxamine Block Co-polymer", FEBS Letters, 400, 319-323 (1997).

M.R.S. Keshtgar and P.J. Ell, "Sentinel Lymph Node Detections and Imaging", Eur. J. Nucl. Med., 26[1], 57-67 (1999).

A.J. Wilhelm, G.S. Mijnhout and E.J.F. Farnssen, "Radiopharmaceuticals in Sentinel Lymph-Node Detection-an Overview", 26, S36-S42 (1999).

C. Tsopelas, "Particle Size Analysis of $^{99m}$Tc-Labeled and Unlabeled Antimony Trisulfide and Rhenium Sulfide Colloids Intended for Lymphoscintigraphic Application", J. Nucl. Med., 42[3], 460-466 (2001).

\* cited by examiner (a)

(b)

(a)

(b)

(a)

(b)

NANOMETER-SIZED CARRIER MEDIUM

CROSS REFERENCE TO RELATED APPLICATION

This claims the benefit of provisional Application No. 60/376,794, filed May 1, 2002, which is incorporated herein it its entirety.

GOVERNMENT LICENSE RIGHTS STATEMENT

The U.S. Government has rights in this invention as provided for by the terms of grant No. DMR 00-79909, awarded by the National Science Foundation.

BACKGROUND OF THE INVENTION

The diagnosis and treatment of a wide variety of medical conditions often involve the introduction of one or more agents into the body of a patient. The effectiveness of procedures that use such agents can often depend on the accuracy of the delivery of the agent to specific anatomical structures of the patient. In diagnostic contexts, for example, signal quality and diagnostic accuracy may be improved by the targeted administration of agents such as contrast media to the structures of interest. In treatment settings, the therapeutic effect of a specific pharmaceutical may be enhanced by the delivery of the pharmaceutical to the particularly affected structures of the body. Such enhancements may also have the added benefit of decreasing the risk of toxicity as lower dosages may be employed without substantial loss of therapeutic benefit.

One approach to the targeted administration of diagnostic or therapeutic agents involves combining the agent with a suitable carrier medium designed to deliver the agent to specific areas of the body of a patient. The specific carrier medium that is suitable in each application is selected for its particular combination of properties which account for the ability of the carrier medium to transport the agent to the structures of interest and to extend the residence time of the agent at such structures. Through the use of a carrier medium, the agent may be selected without regard to its own intrinsic abilities to travel to and remain at specific anatomical structures. As a result of the benefits of targeted administration, the use of a specifically designed carrier medium permits the effective use of a broad array of diagnostic and therapeutic procedures in which agents are used.

The ability of a carrier medium to transport an agent to and remain at a particular anatomical structure of a patient results from the physical and/or chemical properties of the carrier medium. In many applications, a suitable carrier medium is in the form of a two-phase system, such as a colloidal dispersion, comprising a continuous first phase into which a particulate second phase of a controlled size range is dispersed. In such applications, the properties of the colloidal dispersion as a carrier medium are affected by the particle size of the dispersed phase, the ability of the dispersed particles to combine with an agent, and its overall biocompatibility. In view of the specific anatomical structures through which the carrier medium transits and to which it is targeted, it is often desirable to use a dispersed phase having a narrow particle size range. By careful selection of particle size range, the carrier medium may be designed specifically for effective transit through particular vessels and persistent residence at particular anatomical structures.

By way of example, nanometer-sized carriers of a controlled size range are important for size-dependent diagnostic imaging such as imaging of sentinel lymph nodes in connection with the surgical treatment of various forms of cancers such as melanoma and carcinoma of the breast. A significant percentage of patients that present with such cancers show no clinical evidence of metastases while nonetheless harboring occult lymph node metastases. The presence of regional lymph node metastases is a very important predictor of patient survival, and prophylactic elective lymph node dissection has been shown to enhance survival rates when metastases are found.

Lymphoscintigraphy is an imaging technique based on the hypothesis that a melanoma or a breast carcinoma metastasizes to regional lymph nodes via a defined connection of lymphatics. Sentinel lymph nodes are the first lymph nodes in the regional basin which receive direct lymphatic drainage from the primary tumor and which can signal the spread of malignant cells. The absence of cancerous cells in the sentinel lymph nodes is considered to be strongly indicative of the absence of metastases to other nodes in the regional basin. Lymphoscintigraphy is used to image the drainage patterns of the lymphatic system so that sentinel lymph nodes may by located with accuracy. Specific drainage patterns are mapped by the administration of a radioactive colloid at or near the site of the primary tumor. As the colloid transits through the lymphatic system the drainage patterns from the primary lesion are defined and the sentinel lymph nodes may be located. If the sentinel lymph nodes are found negative for metastases, patients may be spared extensive node dissection surgery. If, however, sentinel lymph nodes demonstrate the presence of cancer cells, the patient may be properly identified for complete lymph node dissection and further study. The techniques and details of lymphoscintigraphy as disclosed in U.S. Pat. No. 5,732,704 to Thurston et al. and U.S. Pat. No. 6,205,352 to Carroll are incorporated herein by reference in their entirety.

The need for small and uniform colloidal particles used in lymphoscintigraphy arises from the particular characteristics of the lymphatic system. Particles smaller than about 4 to 5 nm tend to penetrate capillary membranes while large particles, above about 500 nm, become trapped in interstitial spaces or otherwise become stagnant. In either case, such particles do not migrate well through lymphatic channels. For these reasons, it is desirable that particles for sentinel lymph node imaging are uniformly small ranging in size from about 10 to about 200 nm. At present, colloids that have been used in lymphoscintigraphy include $^{99m}$Tc-sulfur, $^{99m}$Tc-albumin, $^{99m}$Tc dextran, $^{99m}$Tc hydroxyethyl starch, $^{99m}$Tc human serum albumin, $^{99m}$Tc-antimony trisulfide, and $^{99m}$Tc-rhenium sulfide. These colloids, however, are not optimal as they lack a narrowly controlled size range and/or require dispersion in an organic continuous phase.

Other related technologies are described in the following publications each of which is incorporated herein by reference in its entirety: W. Stober, A. Fink, and E. Bohn, "Controlled Growth of Monodisperse Silica Spheres in the Micron Size Range," J. Colloid Interface Sci., 26, 62–69 (1968); E. P. Plueddemann, "Silane Coupling Agents," Plenum Press, New York, Chapter 3, 49–73 (1982); A. van Blaaderen, and A. Vrij, "Synthesis and Characterization of Colloidal Dispersions of Fluorescent Monodisperse Silica Spheres," Langmuir, 8 [12], 2921–2931 (1992); K. C. Vrancken, K. Possemiers, P. Van Der Voort, and E. F. Vansant, "Surface Modification of Silica Gel With Ami nooorganosilanes," Colloids and Surfaces, 98, 235–241 (1995); A. E. Hawley, L. Illum, and S. S. Davis, "Lymph Node Localisation of Biodegradable Nanospheres Surface Modified With Poloxamer and Poloxamine Block Co-polymer," FEBS Letters, 400, 319–323 (1997); M. R. S. Keshtgar and P. J. Ell, "Sentinel Lymph Node Detections and Imaging," Eur. J. Nucl. Med., 26[1], 57–67 (1999); A. J. Whilhelm, G. S. Mijnhout, and E. J. F. Farnssen, "Radiopharmaceuticals in Sentinel Lymph-Node Detection—an Overview," 26, S36–S42I (1999); and C. Tsopelas, "Particle Size Analysis of (99m)Tc-Labeled and Unlabeled Antimony Trisulfide and Rhenium Sulfide Colloids Intended for Lymphoscintigraphic Application," J. Nucl. Med., 42[3], 446–451 (2001).

It is known that colloidal silica can possess a narrow size distribution which can be altered easily by varying the parameters of the preparation method. Colloidal silica with a uniform and controlled size is commonly prepared using a sol-gel method. In this process, size-controlled silica particles are obtained through base-catalyzed hydrolysis and condensation. Alkoxysilanes such as tetraethylorthosilicate (TEOS) are hydrolyzed in an alkaline solution including ethanol and water, and silica particles are nucleated homogeneously. The silica particles then grow via consecutive hydrolysis and condensation. The size of silica particles can be controlled by modifications to various reaction conditions such as initial reagent concentration, reaction time, temperature and solvent.

In addition to controlled particle size, carrier media suitable for use in targeting specific anatomical structures must also be able to combine in a stable fashion with the selected diagnostic or therapeutic agent so that effective transport to the structures of interest is realized. One approach has employed the use of silica particles which have been modified with a silane coupling agent such as aminosilane. The amine groups which are bound to the surface of the silica particles enhance the carrying capacity of the particles by providing attachment sites at which the diagnostic or therapeutic agent may be fastened. The amine group is an especially versatile group in providing attachment sites for a wide variety of agents such as imaging materials for use in diagnostic procedures as well as pharmaceuticals and genetic material for use in therapeutic applications.

In diagnostic applications, colloids with agents immobilized on the surface of the particles comprising the dispersed phase are considered "labeled," with the label being the immobilized agent. For example, in applications involving imaging techniques which use various frequencies of light, the label may be a fluorescent agent, for example, a fluorescently-labeled silica colloid. These colloids are prepared in an anhydrous solvent in order to prevent the hydrolysis and condensation of aminopropyltriethoxysilane (APTS), a commonly used silane coupling agent. Such colloids, however, are not suitable for biomedical applications in which an aqueous environment is preferred at near neutral pH.

SUMMARY OF THE INVENTION

According to one aspect of the present invention, there is provided a colloidal dispersion of amine-terminated silica particles having a narrowly controlled size range in an aqueous phase for use in diagnostic imaging, drug delivery and gene therapy. Through controlled particle size range, the ability to anchor at least one diagnostic or therapeutic agent, and the use of an aqueous medium, the colloidal dispersion of the present invention avoids the shortcomings of previous teachings that either lack a narrowly controlled size range or require an organic liquid suspension. In addition, the colloid of the present invention provides a common carrier that is well-suited for anchoring a wide variety of imaging agents, pharmaceuticals and genetic materials.

According to another aspect of the present invention, there is provided a method for preparing surface-modified silica that is suitable for use in an aqueous colloidal carrier medium for size-dependent biomedical applications. The surface modifications permit the silica particles to be coupled with at least one diagnostic or therapeutic agent for suspension in an aqueous phase. Provided in this form, the agent is capable of being used in diagnostic and therapeutic procedures which involve the targeted delivery of an agent to specific anatomical structures.

According to a further aspect of the present invention, there is provided a method for preparing a diagnostic or therapeutic agent for targeted delivery to specific anatomical structures of a patient comprising the step of coupling at least one diagnostic or therapeutic agent with the colloidal dispersion of the present invention. Suitable diagnostic or therapeutic agents include imaging agents, pharmaceuticals and genetic materials.

According to yet another aspect of the present invention, there is provided a method for performing a diagnostic or therapeutic procedure by administration to a patient of at least one diagnostic or therapeutic agent coupled with the colloidal dispersion of the present invention. Suitable procedures for such a method include diagnostic imaging, such as lymphoscintigraphy, as well as drug delivery and gene therapy.

DETAILED DESCRIPTION OF THE INVENTION

Figure 1:
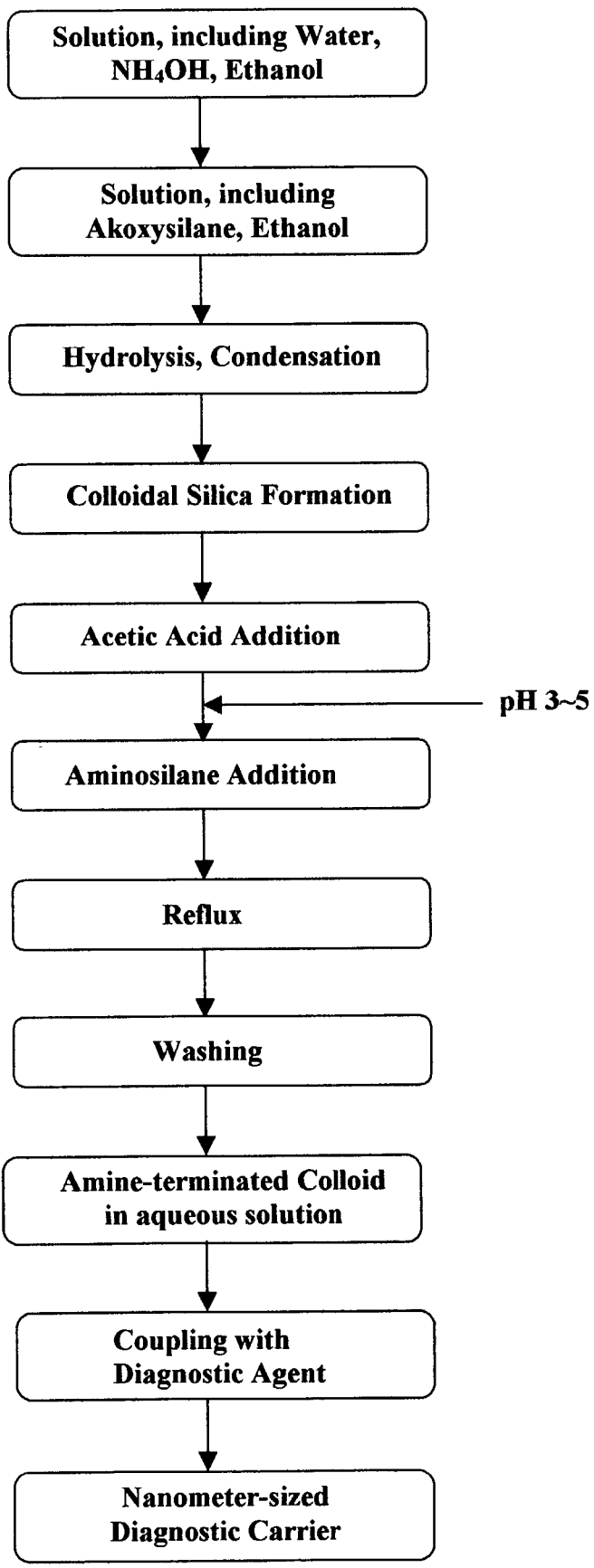
FIG. 1 is a flow chart showing a preferred method of preparing a nanometer-sized carrier medium of the present invention.

The colloidal dispersion of the present invention comprises amine-terminated silica particles having a controlled size range which are dispersed in an aqueous phase. When coupled with a diagnostic or therapeutic agent, the colloidal dispersion provides for the targeted delivery of such agents though transport channels and to the anatomical structures of interest. Suitable agents include imaging materials, targeting molecules or antibodies, biocompatible natural or synthetic molecules such as proteins and peptides, pharmaceuticals, and genetic materials.

The term "colloidal dispersion" as used herein refers to a stable dispersion of discrete silica particles which are modified to carry at least one diagnostic or therapeutic agent and sized to remain suspended in an aqueous phase. Preferably, the colloidal dispersion comprises a particle-containing dispersion that can be applied, such as by pouring, spreading, painting, spraying, atomizing, injecting or inhaling, to reach a certain area or region, and that can subsequently change form by drying or gellation. Therefore, it includes the deposits, films, coatings (dense or porous), gels, droplets and aerosols derived from the colloidal dispersion. The colloidal dispersion of the present invention is particularly well-suited to the targeted delivery of diagnostic and therapeutic agents to specific anatomical structures of a patient.

The term "silica particles" as used herein refers to a plurality of discrete particles of the naturally occurring oxide of silicon having the approximate chemical formula $SiO_2$ without regard to shape, morphology, porosity, and water or hydroxyl content. Preferably, the silica particles are provided in the colloidal dispersion within a narrowly controlled size range so as to facilitate migration pathway control upon administration to a patient. In preferred form, the silica particles have a diameter from about 7 nm to about 200 nm, even more preferably from about 10 nm to about 200 nm. Within this size range, the silica particles possess a sufficiently narrow size distribution that is suitable for the targeted delivery of diagnostic or therapeutic agents to various anatomical structures. Preferably, 95% of the particles are within a range of 20 nm, and all particles within a range of 25 nm. Ultimately, the particular desirable size range depends on the specific anatomical structures involved and the application of use. Colloidal particles as small as 2 nm and as large as 1000 nm may be suitable under certain circumstances. For example, smaller particles are more easily internalized if delivery to the interior of cells is desired.

Silica particles for use in the colloidal dispersion may be prepared in accordance with any technique capable of producing particles within a controlled size range. One preferred technique for preparing silica particles within a controlled size range is a sol-gel process that utilizes base-catalyzed hydrolysis and condensation in an aqueous phase. In preferred form, the sol-gel process involves dispersing an alkoxysilane in an aqueous phase comprising water, $NH_4OH$ and ethanol, and then controlling hydrolysis and condensation to form silica particles within a controlled size range. Other suitable techniques include gas phase synthesis such as gas condensation, chemical vapor condensation, microwave plasma, and combustion flame. In the sol-gel process described above, it is preferred that the pH of the colloidal dispersion of silica particles is adjusted within the range of about 3 to about 5, preferably by the addition of an acid such as acetic acid, hydrochloric acid, nitric acid or sulfuric acid. By controlling pH to within this range, the silica particles may be readily modified by the addition of an amine-bearing coupling agent, such as aminosilane, in order to accommodate the formation of attachment sites on the carrier particles for diagnostic or therapeutic agents.

The term "amine-terminated silica particles" as used herein refers to silica particles in an aqueous colloidal dispersion which have been modified by an amine-bearing coupling agent. The silica particles are modified to provide attachment sites on the silica particles for at least one diagnostic or therapeutic agent. The term "amine-bearing coupling agent" as used herein refers to any biocompatible material which (a) has at least one amine moiety, (b) is capable of modifying the surface of a silica particle by providing the particle at least one attachment site to bind with the agent, and (c) allows the subsequent attachment of at least one diagnostic or therapeutic agent to the amine moiety on the agent. While any biocompatible amine-bearing coupling agent is considered suitable for the modification of silica particles, it is preferred that the amine-bearing coupling agent comprises an aminosilane such as aminopropyltriethoxysilane, aminopropyltrimethoxysilane, aminopropylmethyldiethoxysilane, aminopropylmethyldimethoxysilane, aminoethylaminopropyltrimethoxysilane, aminoethylaminopropyltriethoxysilane, and aminoethylaminopropylmethyldimethoxysilane. It is further preferred that the amine-bearing coupling agent is covalently bonded to the silica particle within the pH range of about 3 to about 5. The amine-terminated silica thus prepared in an aqueous solution have amine group concentrations ranging $1.3 \times 10^{-4}$ mol $NH_2/m^2$ (in SC1, see example below) to $2.2 \times 10^{-4}$ mol $NH_2/m^2$ (in SC3, see example below.) Preferred amine-terminated silica particles readily react with imaging such as fluorescent agents and therapeutic agents that contain an amine-reactive group such as a succinimidyl group, isothiocyanate, carboxylic acid, and sulfonyl chloride. Nanometer-sized, fluorescently or otherwise detectable carriers formed thereby are suitable for use in diagnostic imaging such as sentinel lymph node imaging in connection with the diagnosis and treatment of melanoma or breast cancer. Other imaging agents, targeting molecules or antibodies, biocompatible natural or synthetic molecules such as proteins and peptides, pharmaceuticals, and genetic materials, that contain similar amine-reactive groups can be similarly attached to the amine-terminated silica particles.

One novel feature of the present invention is to prepare amine modified silica particles in an aqueous phase. The term "aqueous phase" as used herein refers to any biocompatible polar liquid that at least partially comprises water which is suitable for use as a suspension medium for amine-terminated silica particles. Preferably, the aqueous phase comprises water or a mixture of water and ethanol.

In the prior art, aminosilanes are preferably coupled to silica in an organic, anhydrous solution, such as toluene. See, e.g., Vrancken et al. Aminosilanes are stable in such a solution under ambient conditions but they can be absorbed to the surface of silica, possibly forming an absorbed monolayer by hydrogen bonding of the amine to a surface hydroxyl group. Covalent bonding is later achieved during curing above 100° C. The reported $NH_2$ concentration on the silica surface typically ranges from 2–3 $NH_2$ molecules/$nm^2$, depending on the surface conditions such as surface hydration and surface structures. See, e.g., Vrancken et al. In an aqueous solution, however, silanol groups have an isoelectric point of about 2–3, and at pH above 7 they tend to gel. Therefore, prior teachings have taught away from using aqueous solutions to couple aminosilanes to silica. It has been unexpectedly found, however, when that such silanol groups are bonded to the silica particles at pH from 3 to 5, the surface concentration of amine groups, always ranging above $10^{-4}$ mol $NH_2/m^2$ (or 60 $NH_2$ molecules/$nm^2$), is at least 20 times higher than the amine group concentrations on silica particle surfaces prepared in a nonaqueous solvent (no higher than 2.8 $NH_2$ molecules/$nm^2$ according FIG. 4 of Vrancken et al.) Using the aqueous solution, amine concentration as high as $2.2 \times 10^{-4}$ mol $NH_2/m^2$ (or 130 $NH_2$ molecules/$nm^2$) can be achieved. Without being bounded by the theory, applicants believe that aminosilanes in a pH range of about 3 to about 5 exist as zwitterions that prevent continuous hydrolysis and condensation reactions. They also exist as oligomers, with a small molecular weight, but with multiple amine groups in one oligomer chain. As a result, when such oligomer chains are bonded to the silica surfaces, multiple amine groups are available from each attachment site. Therefore, surface amine group concentrations ranging from 20 to 40 times higher than that achievable in the prior art can be obtained by using our invention. Since each amine group can be used as an attachment site for an imaging, therapeutic, targeting, or genetic molecule, a higher amine group concentration on the silica particle leads to a larger cargo transported by such carrier.

As used herein, the term "imaging materials" includes biocompatible materials that are either more radiopaque or more radiolucent than surrounding tissues when administered to a patient and include fluorescent dyes, radioactive materials and magnetic materials. As used herein, the term "pharmaceutical" includes any compound intended for the treatment, amelioration or prevention of disease suitable for administration to a patient. The term "genetic material" as used herein includes any material which can be used in connection with gene therapy and includes genomic DNA, cDNA, mRNA, and RNAi including anti-sense RNA and siRNA. Diagnostic and therapeutic agents also include fluorescing agents such as Fluorescein, Rhodamine, and Alexa Fluor®; radioactive agents such as $^{99m}Tc$, $^{125}I$, $^{123}I$; proteins such as Asialoglycoprotein and Circumsporozoite protein; antibodies such as anti-CD 3, anti-CD 5, anti-IgG, vitamins such as folate, and preferably include an amine-reactive derivative such as succinimidyl ester and isothiocyanate which can be attached to $NH_2$-terminated $SiO_2$ in aqueous solution by forming amide and thiourea. An amine-reactive derivative such as sulfonyl chloride is not preferred due to its instability in aqueous solutions.

In those embodiments in which an aminosilane is used as the amine-bearing coupling agent, certain silanes may perform better than others depending on the particular application. For example, for silanes that have a formula $H_2N-R-Si-(OR')_3$ containing a spacer group R between Si and $NH_2$, it may be desirable to vary or select the spacer group. In preferred applications, a spacer group that contains a sufficiently long akyl chain, such as propyl, butyl, pentyl, hexyl, methlyaminopropyl, and ethylaminopropyl, can allow the diagnostic or therapeutic agent that is later attached to the amine group to be sufficiently free of steric interference of the silica particle to perform its functions.

As each transport channel in the body of a patient has a characteristic size, migration of carrier particles along such channel is influenced significantly by the size of the particles. In preferred embodiments, the size range of the silica particles is refined and optimized to permit more accurate delivery of agents through transport channels and to the structures of interest. The accuracy of delivery in diagnostic applications allows for improved image quality and the use of reduced quantities of imaging agents. Imaging methods such as ultrasonic detection, magnetic detection, gamma ray detection, and light including UV, visible, IR, and laser emission detection may advantageously utilize carrier media having particles of a controlled size range. In therapeutic applications, accurate delivery to the affected structures can improve the therapeutic effect and can also permit the use of reduced dosages without substantial loss of such therapeutic benefit. For diagnostic and therapeutic agents which are known to have undesirable side effects, the ability to reduce the quantity of agents administered allows the risk of such side effects to be reduced.

The nanometer-sized carrier medium of the present invention is well-suited for use in a variety of diagnostic and therapeutic procedures in which at least one diagnostic or therapeutic agent is targeted to specific anatomical structures of a patient. By way of example, fluorescent succinimidyl ester compounds may be used as an imaging agent and coupled to the silica particles of the carrier medium of the present invention. These compounds are amine-reactive, water-soluble, and cover a wide range of spectra of absorbance and fluorescent emission. They are thus well-suited for diagnostic imaging utilizing light in a variety of forms including UV, visible, IR and monochromatic laser emission. The diagnostic carrier prepared in this manner is stable in an aqueous environment and biocompatible.

The method of the present invention is directed to the formation of surface-modified silica particles suitable for use in an aqueous colloidal carrier medium for size-dependent biomedical applications. The method preferably involves the preparation of silica particles having a controlled particle size range followed by surface modification of such particles by an amine-bearing coupling agent. The method of the present invention preferably utilizes alkoxysilane, ammonia, water and ethanol as starting materials in a sol-gel process to form the silica particles within a controlled size range, and the subsequent addition of aminosilane under acidic conditions to modify the surface of the silica particle. The silica particles are modified by the amine-bearing coupling agent forming attachment sites for a diagnostic or therapeutic agent. The colloidal dispersion of amine-terminated silica particles in an aqueous phase prepared by such method is well-suited as a carrier medium for diagnostic or therapeutic agents coupled thereto. The colloidal dispersion remains stable in an aqueous environment, is biocompatible, and can be administered into the body of a patient in a variety of diagnostic and therapeutic applications.

The method of the present invention may further comprise refluxing the water-stable amine-terminated silica colloid in order to covalently bind silica with aminosilane. Preferably, the colloid is refluxed at 80° C. for 3hr. The method may further comprise washing the refluxed colloid in order to remove the unreacted agents. Preferably, the colloid is washed by centrifugation or dialysis at room temperature.

EXAMPLES

A preferred method of preparing surface-modified silica suitable for use in an aqueous colloidal carrier medium is described herein as shown in the flow chart depicted in FIG. 1 and in accordance with the reaction conditions for preparing three differently sized colloidal carrier media as shown in Table 1.

TABLE 1

| Silica colloids prepared by sol-gel process | | | | | |
|---|---|---|---|---|---|
| Sample | TEOS | NH$_4$OH | H$_2$O | Particle Size (SC) | Particle Size (NH$_2$—SC) |
| SC-1 | 0.2 M | 0.25 M | 1 M | 28 nm | 34 nm |
| SC-2 | 0.2 M | 0.5 M | 2 M | 58 nm | 67 nm |
| SC-3 | 0.2 M | 0.5 M | 3 M | 111 nm | 109 nm |

Figure 2:
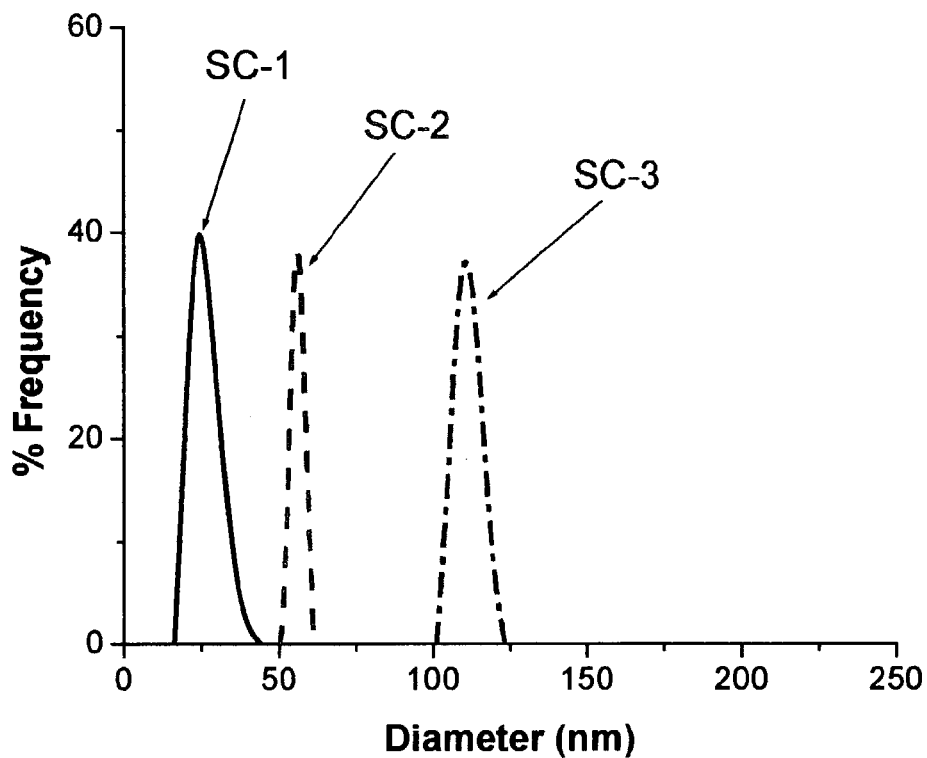
FIG. 2 is a particle size distribution of (a) silica colloids and (b) amine-terminated silica colloids.
Figure 2:
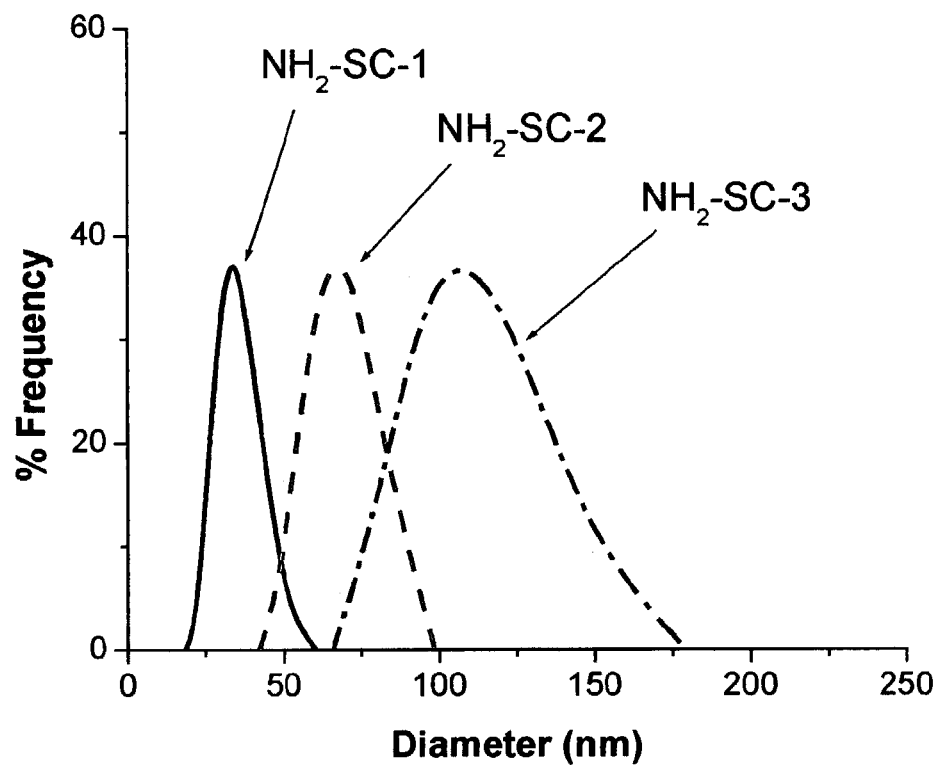

In accordance with this preferred method, TEOS is first added to ethanol to which is then added a mixture of NH$_4$OH (29.5 wt. %), H$_2$O and ethanol, wherein the NH$_4$OH is used as a basic catalyst. The solution is stirred at room temperature for 15 hours. As shown in FIG. 2, particle size varies from 28 nm, 58 nm to 111 nm which is achieved by varying the concentration of solutions as shown in Table 1. The particle size shown in FIG. 2 and Table 1 was measured with a light scattering photon correlation spectroscope identified as a Zetasizer 3000HS$_A$ by Malvern. The resulting silica colloid is adjusted with 1M acetic acid to a pH of 4 in order to prevent hydrolysis and condensation upon addition of the amine-bearing coupling agent.

In order to modify the surface of the silica particles, 2 cc of APTS or aminopropylsilane (APS) is added to 50 cc of the silica colloid and then stirred at room temperature for 1 hour. The colloid is refluxed at 80° C. for 3 hours and then washed three times by dialysis. The amine groups form a thin layer of amine terminations on the surface of the silica. FIG. 2 compares the particle sizes and the size distributions before and after the coupling of the amine groups on the particle surface. Despite some broadening, the size of the silica particles can still be narrowly controlled over a range of about 10 nm to about 200 nm.

The amine-terminated silica prepared in this fashion was examined to determine whether the amine group is covalently bonded to the silica in order to assess the ability of carrier to securely attach agents thereto for effective transport to anatomical structures of interest. In accordance with the examination procedure, the amine group on the silica particles is first reacted with salicylic aldehyde. After the reaction, the color of the colloid is changed to bright yellow and its absorbance spectrum reveals a new peak at about 404 nm when measured with a UV/visible spectrometer identified as a DU® series 600 sold by Bechman Coulter. This absorbance peak is characteristic of salicylic aldehyde. To determine whether the salicylic aldehyde is attached to the silica particles or is in solution, the colloidal solution is separated using a centrifuge to obtain a solution substantially free of colloidal particles which does not show an absorbance peak at about 404 nm. The absence of an absorbance peak at about 404 nm indicates that free or unbonded amine groups are not present in solution.

Figure 3:
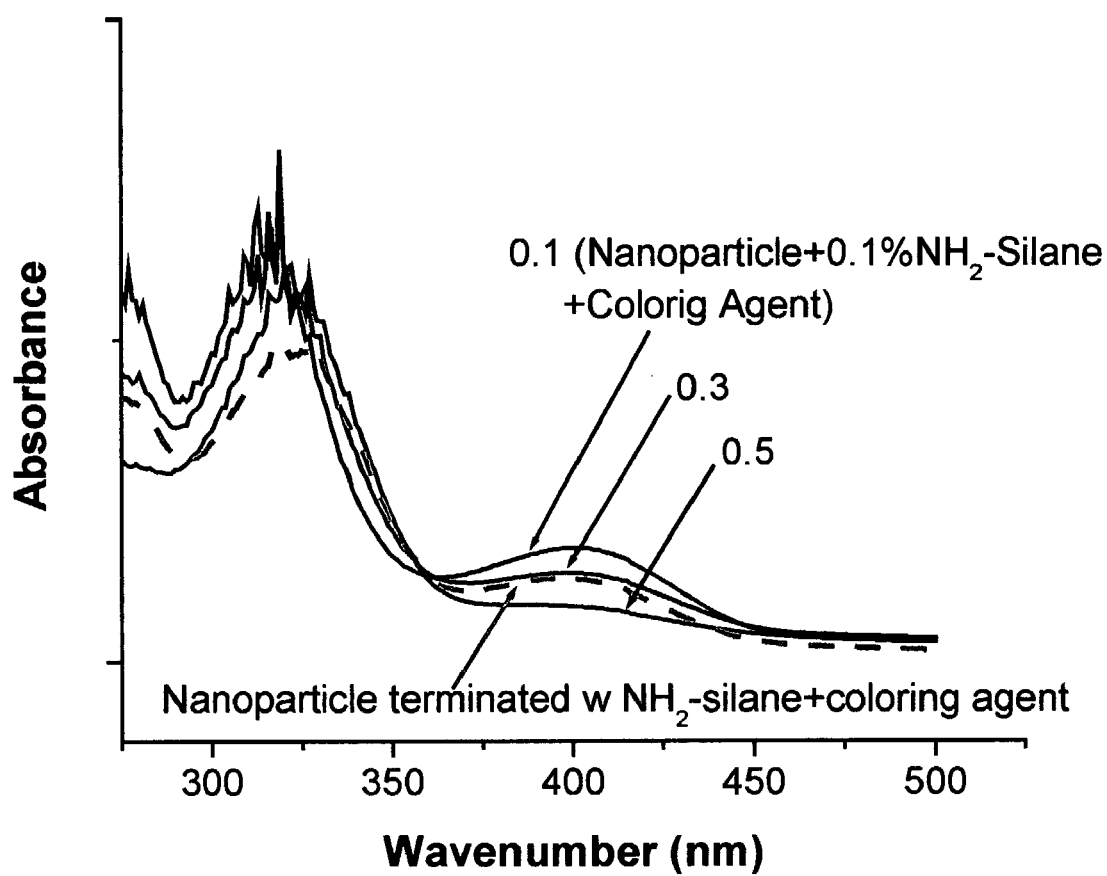
FIG. 3 shows UV-Visible spectra for the quantification of free amine groups exposed on the surface of nanometer-sized particles.

The amount of amine groups on the surface of silica particles can be quantified as shown in FIG. 3 using a set of calibrated colloids which contain three different concentrations of unreacted silica particles with unmodified surfaces, unreacted silane free in the solution, and unreacted salicylic aldehyde free in the solution. Using the calibration curves thus obtained, the amount of amine concentration on the surface of the silica particles is determined to be $1.3 \times 10^{-4}$ mol $NH_2/m^2$ on $NH_2$ (as in SC1) to $2.2 \times 10^{-4}$ mol $NH_2/m^2$ on $NH_2$ (as in SC3).

Figure 4:
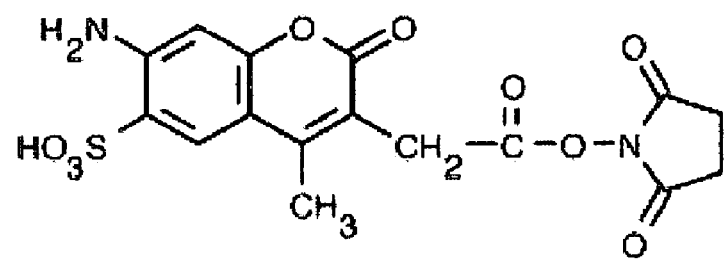
FIG. 4 is the molecular structure of Alexa Fluor® 350 succinimidyl ester.
Figure 5:
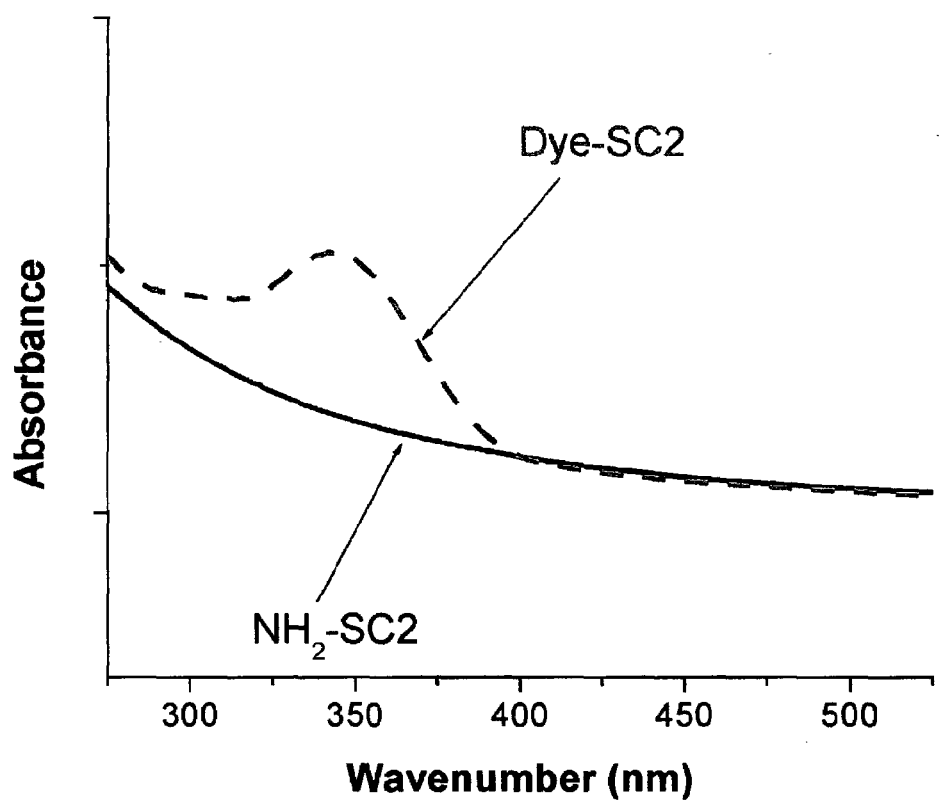
FIG. 5 shows a comparison of two colloids before and after coupling with fluorescent dye by (a) UV-Visible spectra and (b) particle size distribution.
Figure 5:
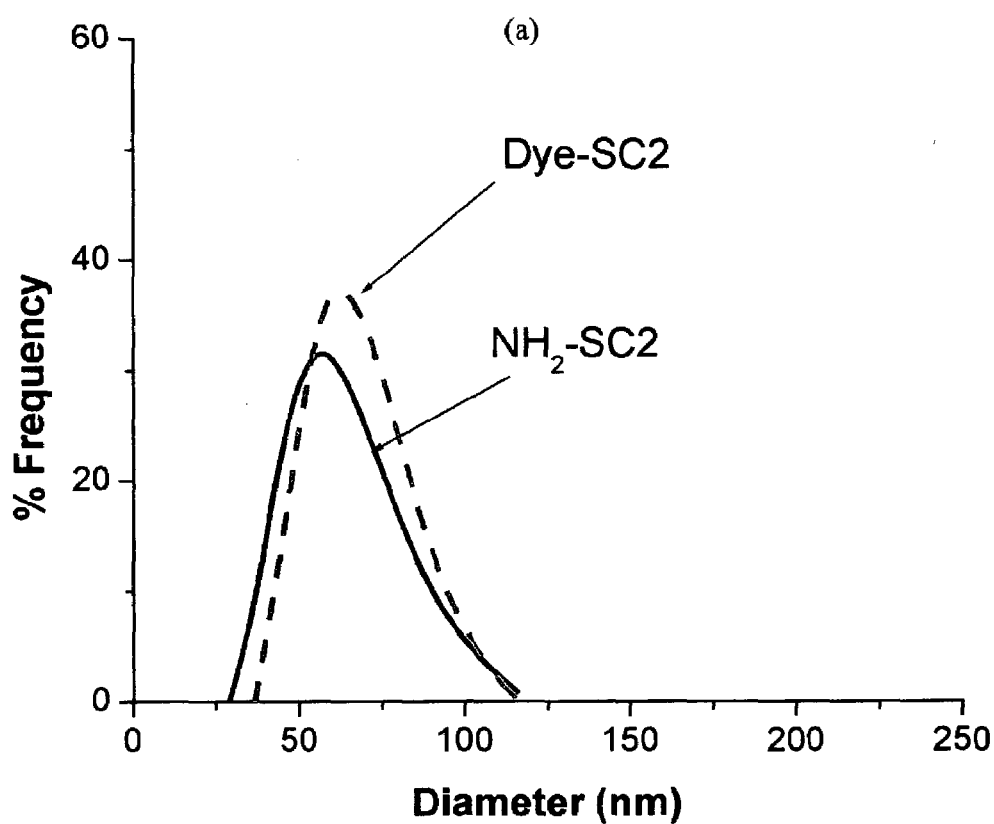
Figure 6:
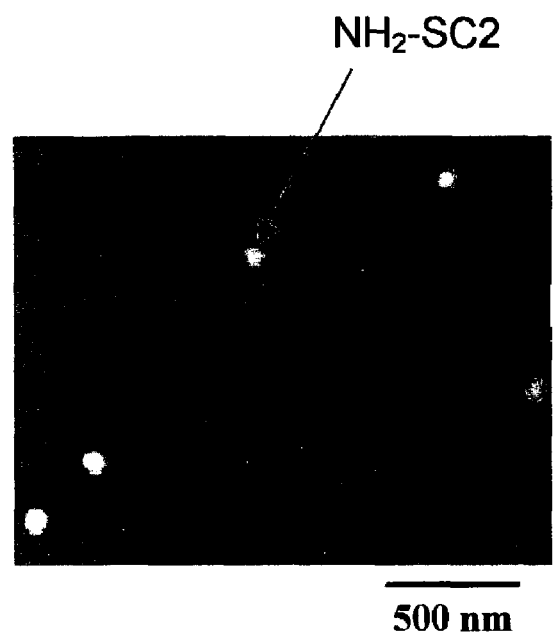
FIG. 6 shows atomic force microscopy images of the colloids (a) before and (b) after dye attachment
Figure 6:
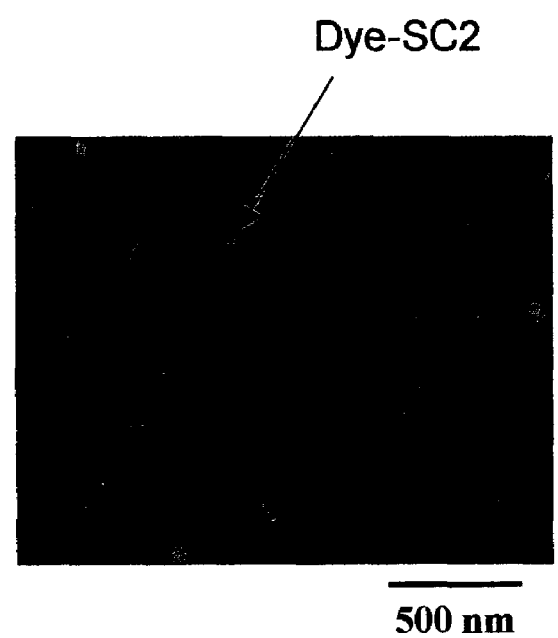

The amine-terminated silica may be incorporated with at least one diagnostic or therapeutic agent a fluorescent dye such as, for example, succinimidyl ester sold under the trademark Alexa Fluor® 350 by Molecular Probes. FIG. 4 shows the molecular structure of the dye. The absorbance and the fluorescence emission of the dye have maxima at 346 nm and 442 nm. This succinimidyl ester derivative is water-soluble and reactive with amines. To prepare the reaction, 0.5 mg Alexa Fluor® 350 is mixed in 2 cc of water. The dye solution is added to 8 cc of the amine-terminated silica colloid. After stirring for 3 hours followed by washing, a dye-coupled colloidal carrier medium is obtained. To verify that the dye has been attached to the silica particles and is active, the carrier including fluorescent dye is observed using a UV-visible spectrometer which reveals an absorbance peak at 346 nm as shown in FIG. 5a. The final particle size is very similar to the size prior to dye attachment as shown in FIG. 5b. There appears to be no significant increase or broadening of the particle size. To verify this finding and to illustrate the general spherical geometry of the silica particles, atomic force microscopy images of the colloids before and after dye attachment are shown in FIG. 6. As a result, carrier particles with diagnostic imaging agents such as dyes attached thereto may be controlled for size between about 10 nm and about 200 nm.

We claim:

1. A colloidal dispersion comprising amine-terminated silica particles having a narrowly controlled size range dispersed in an aqueous phase capable of coupling with at least one diagnostic or therapeutic agent for administration to a patient, wherein the amine-terminated silica particles have a diameter from about 7 nm to about 200 nm and wherein the amine-terminated silica particles are obtained by modifying the surface of silica particles with an amine-bearing coupling agent in an intermediate aqueous phase, and wherein the amine-terminated silica particles have a surface concentration of amine groups of above 60 $NH_2$ molecules/$nm^2$.

2. The colloidal dispersion of claim 1 wherein the silica particles have a diameter of about 10 to about 200 nm.

3. The colloidal dispersion of claim 1 wherein about 95% of the silica particles range in size by about 20 nm.

4. The colloidal dispersion of claim 1 wherein the silica particles are formed by hydrolysis and condensation.

5. The colloidal dispersion of claim 1 wherein the silica particles are modified by the addition of an amine-bearing coupling agent under acidic conditions.

6. The colloidal dispersion of claim 5 wherein the amine-bearing coupling agent is an anaminosilane selected from the group consisting of aminopropyltriethoxysilane, aminopropyltrimethoxysilane, aminopropylmethyldiethoxysilane, aminopropylmethyldimethoxysilane,aminoethylaminopropyltrimethoxysilane, aminoethylaminopropyltriethoxysilane, and aminoethylaminopropylmethyldimethoxysilane.

7. The colloidal dispersion of claim 5 wherein the silica particles have an amine concentration of about $1.0 \times 10^{-4}$ mol $NH_2/m^2$ to about $3 \times 10^{-4}$ mol $NH_2/m^2$.

8. The colloidal dispersion of claim 1 wherein the aqueous phase comprises water, $NH_4OH$ and ethanol.

9. The colloidal dispersion of claim 1 further comprising at least one diagnostic or therapeutic agent coupled thereto.

10. The colloidal dispersion of claim 9 wherein the diagnostic or therapeutic agent comprises an amine-reactive derivative wherein the amine-reactive derivative is a member selected from a group consisting of isothiocyanate, succinimidyl ester, and carboxylic acid.

11. The colloidal dispersion of claim 9 wherein the agent is a contrast medium for use in diagnostic imaging procedures.

12. The colloidal dispersion of claim 9 wherein the agent is a pharmaceutical compound.

13. A method for preparing the silica particles of claim 1 suitable for use in an aqueous colloidal carrier medium comprising the step of modifying the surface of silica particles provided within a narrowly controlled size range with an amine-bearing coupling agent in an aqueous phase having a pH between about 3 and about 5.

14. The method of claim 13 wherein about 95% of the silica particles range in size by about 20 nm.

15. The method of claim 13 wherein the silica particles are formed to a controlled size by hydrolysis and condensation.

16. The method of claim 13 wherein the amine-bearing coupling agent is aminosilane selected from the group consisting of aminopropyltriethoxysilane, aminopropyltrimethoxysilane, aminopropylmethyldiethoxysilane, aminopropylmethyldimethoxysilane,aminoethylaminopropyltrimethoxysilane, amino ethylaminopropyltriethoxysilane, and aminoethylaminopropylmethyldime-thoxysilane.

17. The method of claim 13 wherein the aqueous phase comprises water, $NH_4OH$ and ethanol and an acid selected from the group consisting of acetic acid, hydrochloric acid, nitric acid and sulfuric acid.

18. A method for preparing a diagnostic or therapeutic agent for targeted delivery to specific anatomical structures of a patient comprising the step of coupling at least one diagnostic or therapeutic agent with the colloidal dispersion of claim 1.

19. The method of claim 18 wherein the agent is suitable for use in imaging a lymphatic system of the patient.

20. A method for performing a diagnostic or therapeutic procedure by administration to a patient of at least one diagnostic or therapeutic agent coupled with the colloidal dispersion of claim 1.

21. The method of claim 20 wherein the agent is suitable for use in imaging a lymphatic system of the patient.

22. The colloidal dispersion of claim 9, wherein the amine-terminated silica particles are obtained by modifying the surface of silica particles with the amine-bearing coupling agent in the intermediate aqueous phase under acidic conditions.

23. The colloidal dispersion of claim 22, wherein the amine-terminated silica particles are obtained by modifying the surface of silica particles with the amine-bearing coupling agent in the intermediate aqueous phase having a pH between about 3 and about 5.

24. The colloidal dispersion of claim 9, wherein about 95% of the silica particles range in size by about 20 nm.

\* \* \* \* \*